United States Patent
Niino et al.

(12) 
(10) Patent No.: US 6,211,953 B1
(45) Date of Patent: Apr. 3, 2001

(54) VESSEL FOR IMAGING FLUORESCENT PARTICLES

(75) Inventors: Masao Niino; Hiroki Matsui; Akio Komatsu, all of Gamagori (JP)

(73) Assignee: Kowa Company Ltd. (JP)

( * ) Notice: Subject to any disclaimer, the term of this patent is extended or adjusted under 35 U.S.C. 154(b) by 0 days.

(21) Appl. No.: 09/213,762

(22) Filed: Dec. 17, 1998

(30) Foreign Application Priority Data

Dec. 25, 1997 (JP) .................................................. 9-356416

(51) Int. Cl.[7] ............................ G01N 21/03; G01N 21/64
(52) U.S. Cl. ........................................ 356/246; 250/458.1
(58) Field of Search ....................... 356/246; 250/461.1, 250/461.2, 458.1; 422/82.08, 942

(56) References Cited

U.S. PATENT DOCUMENTS

| Re. 32,598 | * | 2/1988 | White | 250/458.1 |
| 5,225,164 | * | 7/1993 | Astle | 356/246 |
| 5,355,215 | * | 10/1994 | Schroeder et al. | 250/461.2 |
| 5,457,527 | * | 10/1995 | Manns et al. | 356/246 |

* cited by examiner

*Primary Examiner*—F. L. Evans
(74) *Attorney, Agent, or Firm*—Adams & Wilks (57) ABSTRACT

A vessel for imaging fluorescent particles comprises a tubular body having an upper section, and a lower section defining an interior space for containing fluorescent particles. The lower section of the tubular body has an exterior surface portion forming an entry surface for transmitting into the interior space a beam of light projected in a direction generally parallel to the exterior surface portion of the lower section to illuminate the fluorescent particles.

10 Claims, 9 Drawing Sheets

VESSEL FOR IMAGING FLUORESCENT PARTICLES

BACKGROUND OF THE INVENTION

1. Field of the Invention

This invention relates to a vessel for imaging fluorescent particles, and more particularly to a vessel for holding fluorescent particles such as leukocytes or the like stained with a fluorescent dye for imaging the fluorescent particles.

2. Description of the Prior Art

In the medical field, platelet preparations and erythrocyte preparations are produced by extracting platelets and erythrocytes from whole blood. These platelet and erythrocyte preparations are each used for blood transfusions, and it is undesirable for either preparation to contain leukocytes. It is therefore important to be able to know how many leukocytes the preparations contain. Conventionally this is done by placing a sample platelet preparation in a NAGEOTTE chamber, staining with a fluorescent dye, projecting an excitation light onto the sample and counting leukocytes via a microscope. Specifically, a 50 microliter sample is taken from a 200 or 400 milliliter bag of platelet preparation, the leukocytes in the sample are counted and converted to a leukocytes count for the whole bag. This is a tiring, inefficient, time-consuming task that has to be done by skilled personnel.

An apparatus has been proposed to enable leukocytes to be counted, instead, by staining the leukocytes with a fluorescent dye, illuminating the sample with an excitation light having predetermined wavelengths, using a CCD camera or the like to image the sample and then analyzing the images to obtain a count of the leukocytes. However, the solution containing the stained leukocytes also contains fluorescent dye that also emits fluorescent light. Thus, since not only the stained leukocytes but also the fluorescent dye itself is excited by the excitation light, there is a marked decrease in the contrast of the leukocytes that it is desired to observe or image. In some cases, the contrast may worsen to the point that the leukocyte images become so buried in the background that they cannot be picked out, making it impossible to count the leukocytes.

An object of the present invention is to provide a vessel for containing fluorescent particles that enables the fluorescent particles to be well imaged by reducing the effect of background light.

SUMMARY OF THE INVENTION

To attain the above object, the present invention provides a vessel for imaging fluorescent particles that are stained with fluorescent dye and illuminated by excitation light, the fluorescent particles being contained in a bottom portion of the vessel and imaged from below the bottom portion, wherein part of the exterior surface of the bottom portion is formed to be an excitation light entry surface.

In accordance with this arrangement, as the fluorescent particles that are the object of interest are accumulated in the bottom part of the imaging vessel and the bottom portion of the vessel has an external side face that is an entry surface for the excitation light, only the bottom portion of the vessel is illuminated by the excitation light, so background light can be reduced, thereby making it possible to obtain high-contrast images of the fluorescent particles in the vessel.

Background light can be further reduced by a considerable amount by using a shield member to cover parts of the imaging vessel other than the vicinity of the bottom portion.

It is preferable to form the bottom portion so that it has a square or rectangular horizontal cross-section with one side thereof forming an excitation light entry surface. The bottom portion may also be given a horizontal cross-section having a round shape, and a negative cylindrical lens disposed on the side from which the bottom portion is illuminated by the excitation beam.

Further features of the invention, its nature and various advantages will become more apparent from the accompanying drawings and following detailed description of the invention.

DESCRIPTION OF THE PREFERRED EMBODIMENTS

Figure 1:
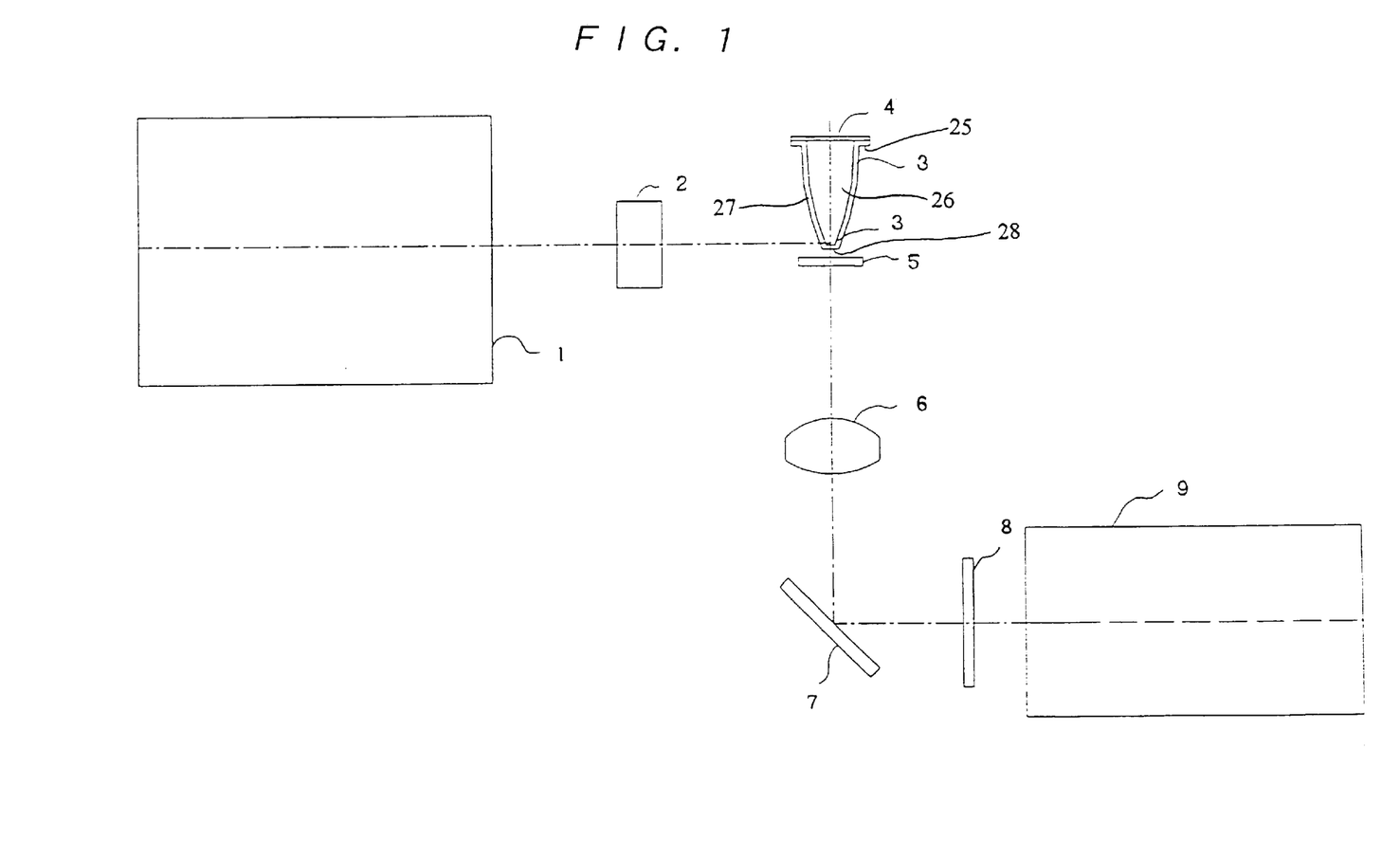
FIG. 1 is a block diagram showing the general configuration of an apparatus for imaging fluorescent particles according to the present invention.
Figure 2:
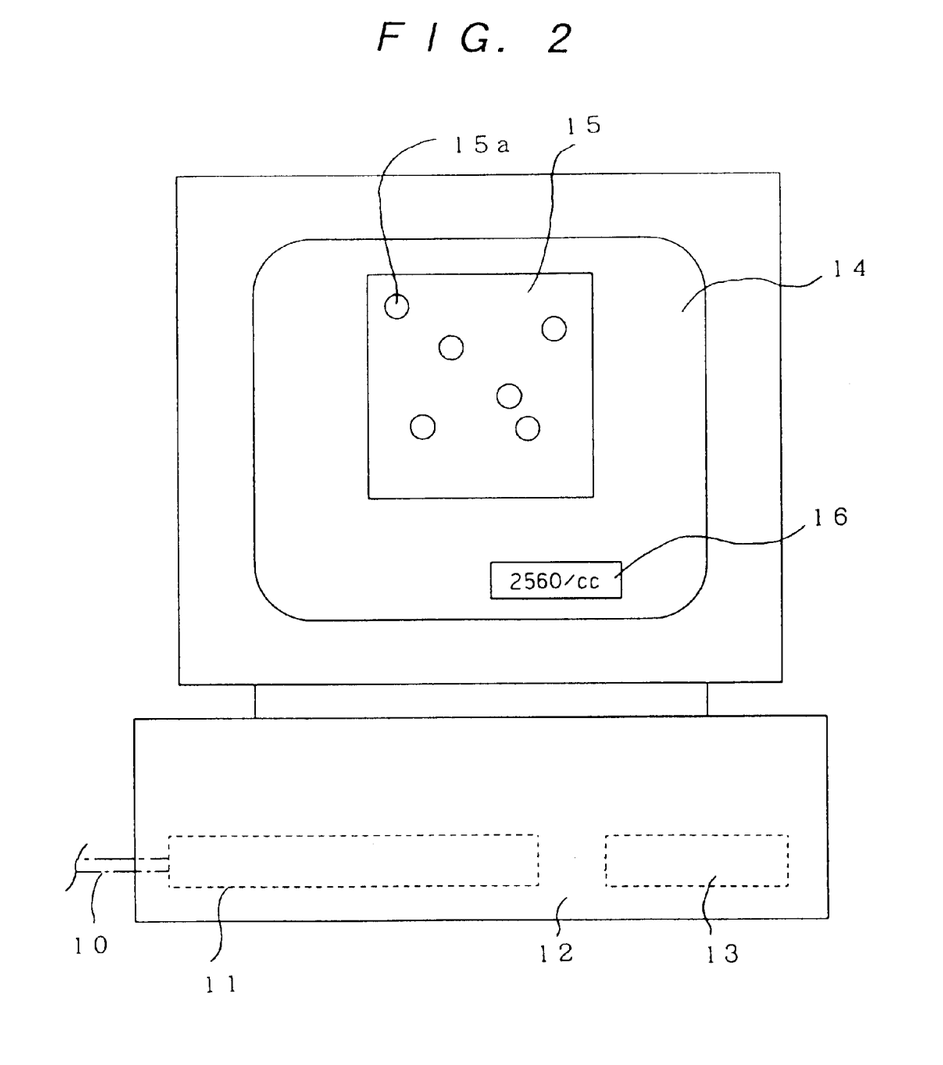
FIG. 2 is a front view of the apparatus used for analyzing and displaying obtained fluorescent particle images.

FIGS. 1 and 2 show the arrangement of a first embodiment of the present invention. In the drawings, reference numeral 1 denotes a laser light source, such as, for example, a YAG laser that produces a green laser beam. The laser beam from the laser light source 1 impinges upon, and is diffused by, a diffusion plate 2 comprised of ground glass or other such member that is able to diffuse light. The light thus diffused is projected at a bottom section or portion 3' of an imaging vessel which has a generally tubular body, the upper part of which is covered by a cover 4. The bottom portion 3' has a side wall 27 and a bottom wall 28. Fluorescent particles are accumulated in an interior space 26 at the bottom portion of the imaging vessel 3, and these fluorescent particles fluoresce when illuminated by the laser beam. The images of the fluorescent particles illuminated by the laser beam pass via a cover-glass 5 and objective lens 6 to a mirror 7 that reflects the images to a barrier filter 8 that transmits light in a prescribed frequency band, and are then picked up by a CCD camera 9.

The images of the fluorescent particles picked up by the CCD camera 9 are passed via a signal line 10 to a video capture device 11 of a computer 12, where they are processed by an image processing circuit 13 (FIG. 2) to enable the fluorescent particles to be recognized. There is a change in brightness where there is a fluorescent particle, so the fluorescent particles can be recognized by, for example, using the differentiation of signal values to detect the positional coordinates of the particles. The fluorescent particles thus recognized are displayed on a monitor 14. FIG. 2 depicts the image 15 of the bottom portion of the vessel together with a plurality of fluorescent particles 15a therein, displayed on the monitor 14. The fluorescent particles 15a are counted and the count is also displayed at the lower part 16 of the monitor 14.

The imaging vessel 3 is molded in one piece from transparent polystyrene resin, glass, or acrylic resin, preferably polystyrene resin. Inserted into the imaging vessel 3 are a platelet preparation sample (100 microliters, for example), a chemical (Triton X) that dissolves platelet and leukocyte cytoplasm, and a fluorescent dye (propidium iodide) for staining leukocyte nuclei. The imaging vessel 3 is then subjected to centrifugal separation in a centrifuge (not shown), causing the leukocyte nuclei to collect in the bottom portion of the imaging vessel 3. All of the leukocyte nuclei can be collected in the bottom portion 3' of the imaging vessel 3 by applying a prescribed centrifugal force.

The cover 4 is then used to cover the imaging vessel 3 in which the leukocyte nuclei stained with a fluorescent dye are collected in the bottom portion 3' thereof, and the imaging vessel 3 is mounted on the imaging apparatus. For imaging, the laser light source 1 is activated, producing a laser beam which is diffused by the diffusion plate 2 and projected onto the bottom portion 3' of the imaging vessel 3. As the nuclei of the leukocytes in the bottom portion 3' of the imaging vessel 3 have been stained with a fluorescent dye, when they are illuminated by the beam of excitation light, they emit fluorescent light having a frequency of around 600 nm. This is picked up via the cover-glass 5, objective lens 6, mirror 7 and barrier filter 8 below the imaging vessel 3. The barrier filter 8 only transmits light having the frequency of fluorescent light, allowing light of harmful frequencies to be blocked at this point.

The laser beam is projected only at the bottom portion of the vessel, effectively illuminating the leukocytes collected there. Therefore, even if there is fluorescent dye floating in the solution in the imaging vessel 3, it is possible to prevent the fluorescent dye from forming harmful background light, thereby enabling the images to be obtained with improved contrast.

With reference to FIG. 2, the images of fluorescent particles thus obtained by the CCD camera 9 are passed via a signal line 10 to a video capture device 11 of a computer 12, where they are processed by an image processing circuit 13 to count the number of leukocytes 15a.

Figure 3:
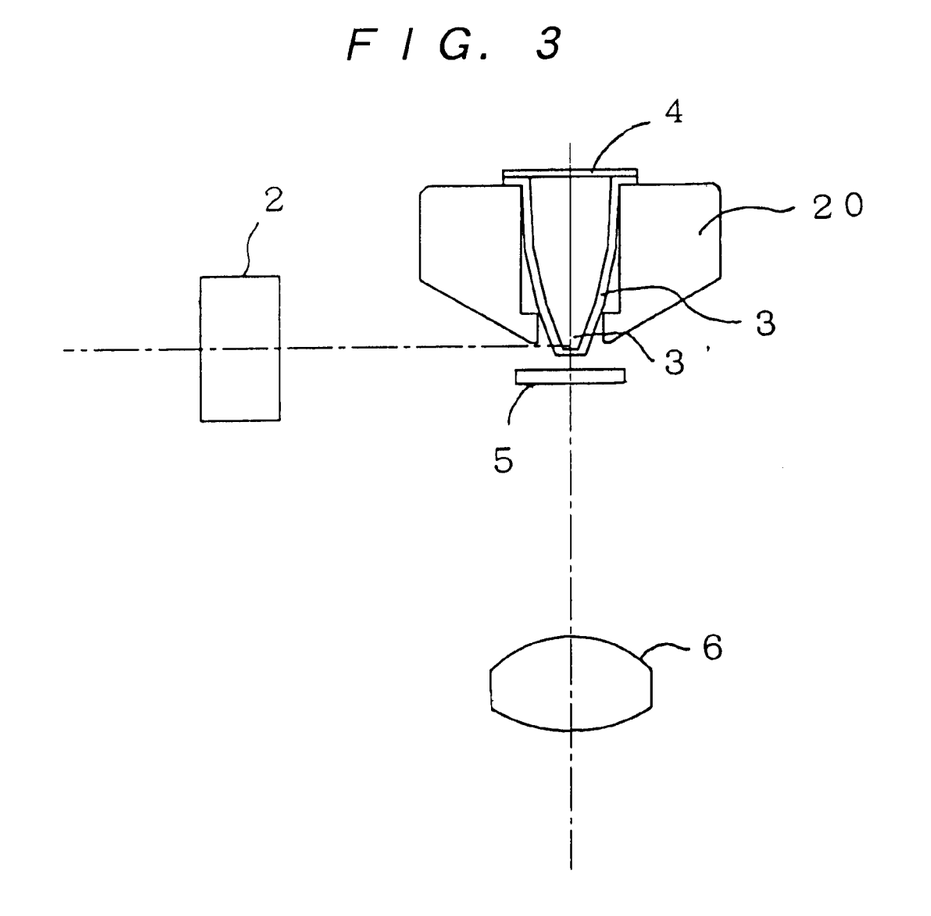
FIG. 3 is a diagram illustrating an arrangement of a cover used to shield the upper part of the imaging vessel.

In accordance with the arrangement described above, the laser beam is projected only onto the bottom portion of the imaging vessel and does not illuminate the upper part of the vessel. As shown by FIG. 3, the effect of only illuminating the bottom portion can be enhanced by providing a cover 20 that shields all parts other than the bottom portion from the illuminating light beam.

Figure 4:
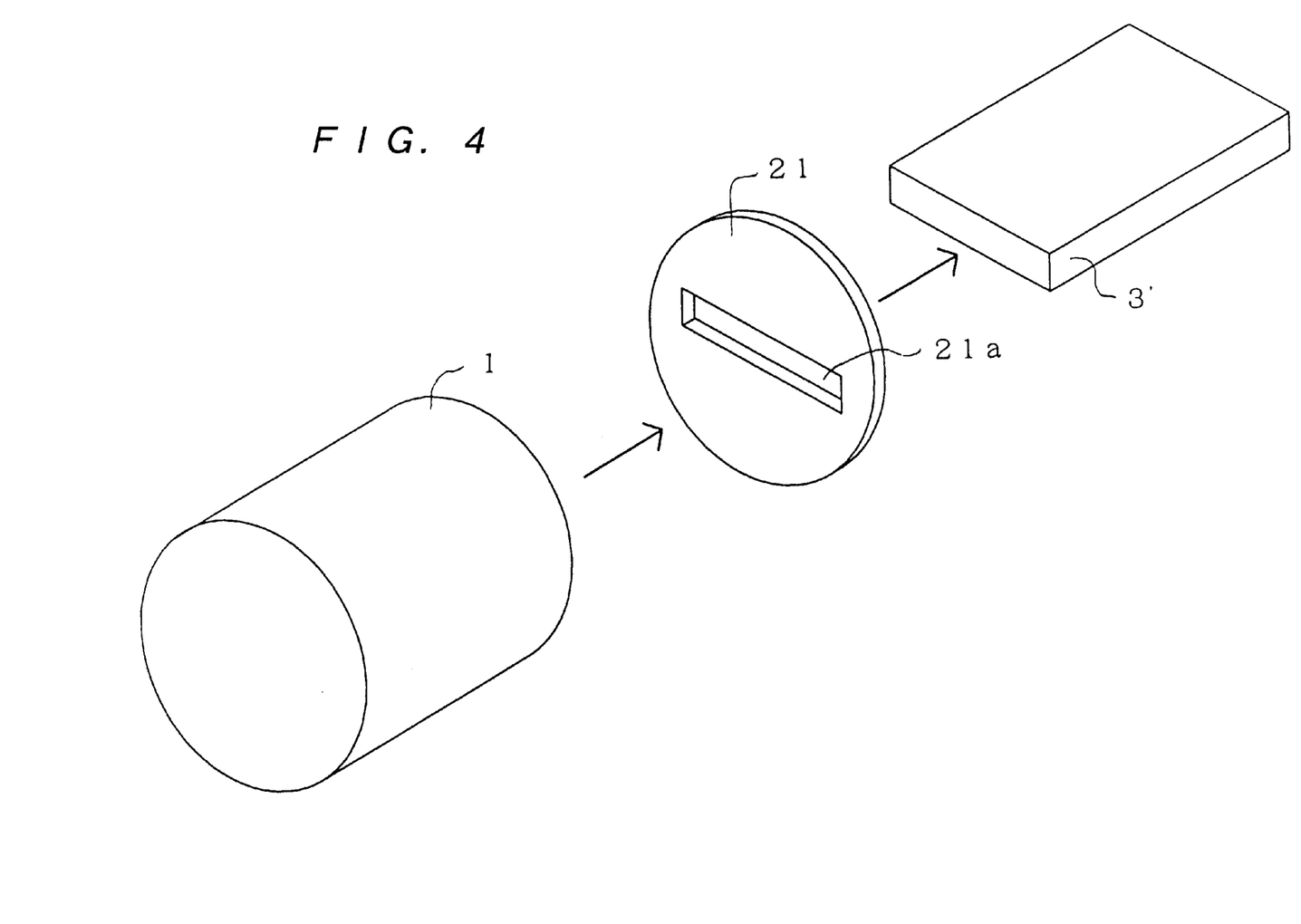
FIG. 4 is a diagram illustrating another arrangement for shielding the upper part of the imaging vessel from illuminating light.

Instead of the cover arrangement of FIG. 3, an arrangement such as that shown in FIG. 4 may be used. In this arrangement, a mask 21 having a central slit-shaped aperture 21a is used. The laser beam from the laser light source 1 passes through the aperture 21a, ensuring that only the bottom portion 3' of the imaging vessel 3 is illuminated.

Figure 5:
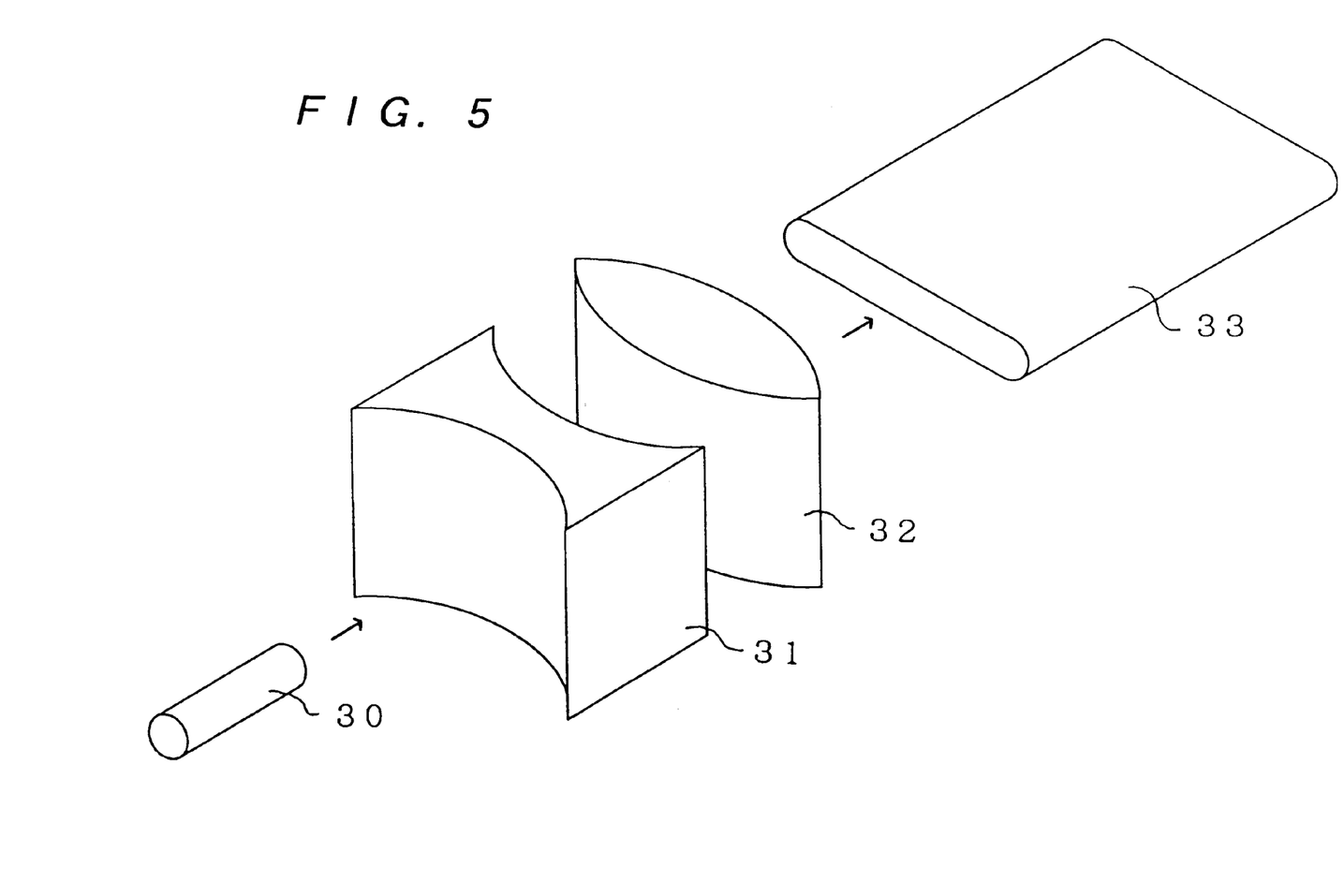
FIG. 5 is a diagram of an optical system used to form a strip-shaped excitation light beam.

A linear or line-shaped light beam would illuminate more of the bottom portion of the imaging vessel than a spot-shaped beam. FIG. 5 shows the type of arrangement that could be used in such a case, with laser beam 30 being shaped to a flat beam 33 by passage through cylindrical lenses 31 and 32, and the flat beam 33 being used to illuminate the bottom portion 3' of the imaging vessel 3 by projecting the flat bean 33 in a direction generally parallel to the bottom wall 28 of the bottom portion 3'.

Figure 6:
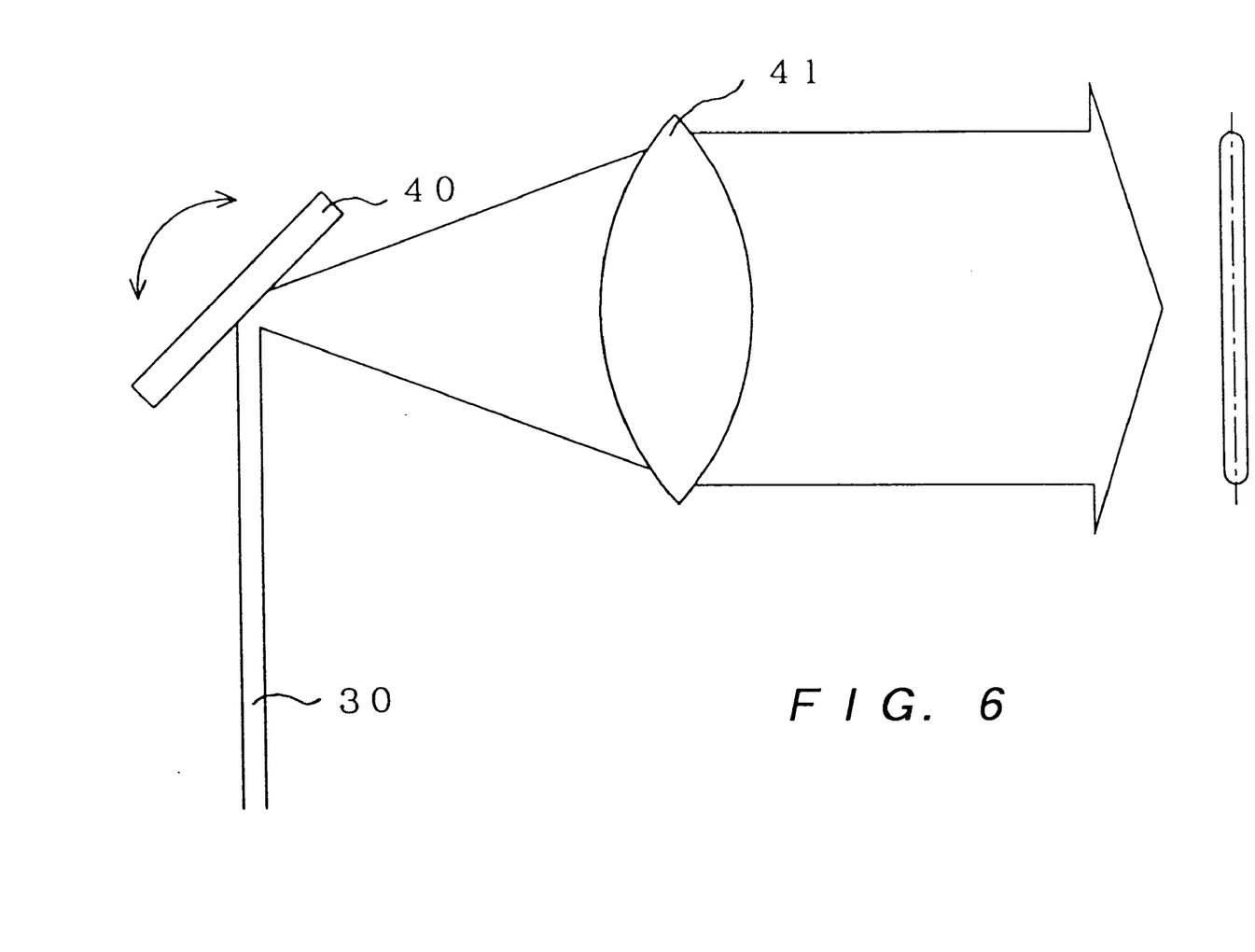
FIG. 6 is a diagram of another optical system used to form a strip-shaped excitation light beam.

FIG. 6 shows another arrangement, in which a scanning mirror 40 is used to deflect the laser beam 30, which passes through a lens 41 to scan the bottom portion of the imaging vessel.

Figure 7:
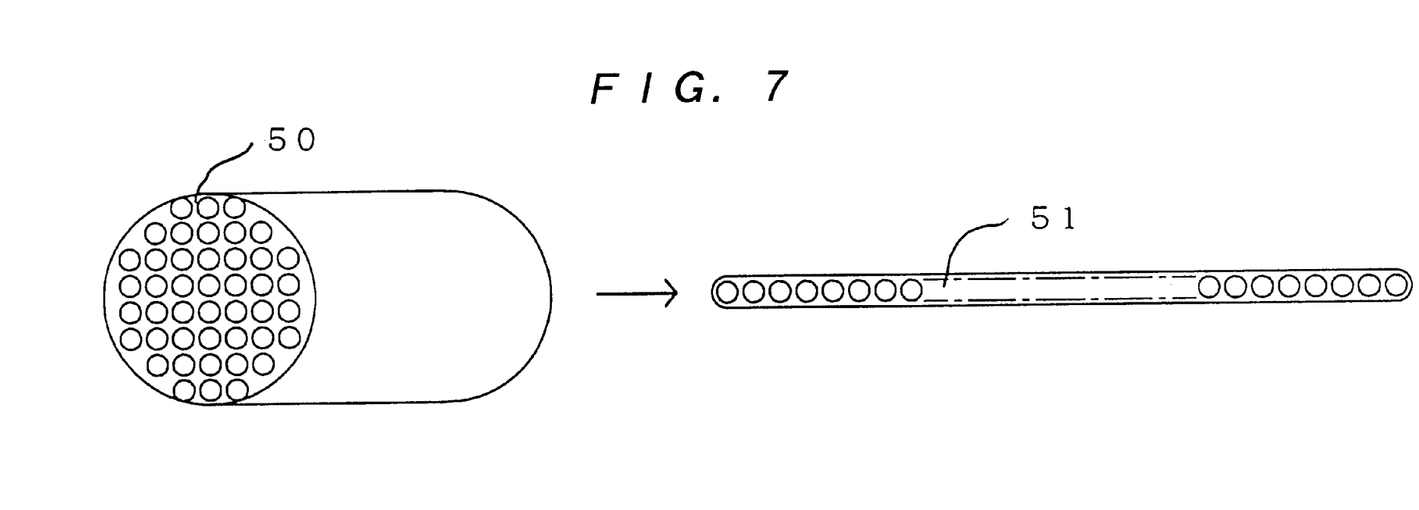
FIG. 7 is a diagram showing the configuration of optical elements used to form a strip-shaped excitation light beam.

FIG. 7 shows another arrangement, that uses a bundle of optical fibers. In this arrangement, the fibers at the entrance end 50 from which the laser beam enters are arranged in a round configuration, while at the exit end 51 the fibers are arranged in a straight line, with the exit end 51 being disposed in the vicinity of the bottom portion of the imaging vessel so as to illuminate the bottom portion thereof.

In each of these embodiments, only the bottom portion of the vessel, or the vicinity thereof, is illuminated, by a strip-shaped beam, thereby making it possible to obtain images of the fluorescent particles with good contrast. Moreover, if a diffusion plate 2 is used to diffuse the laser beam, it enables the bottom portion of the imaging vessel to be illuminated uniformly.

Figure 8A:
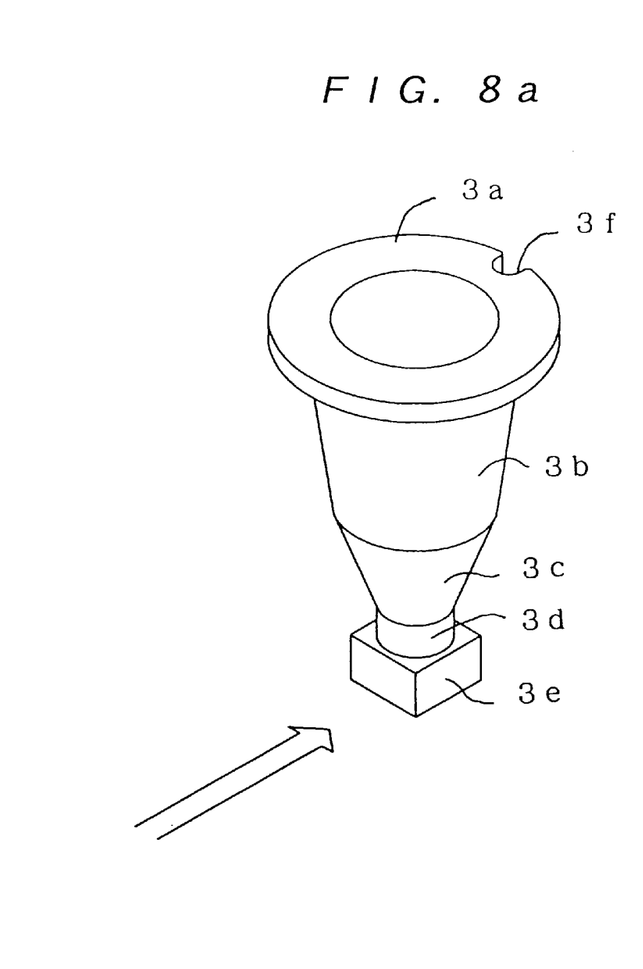
FIG. 8a is an exterior perspective view of the imaging vessel.
Figure 8B:
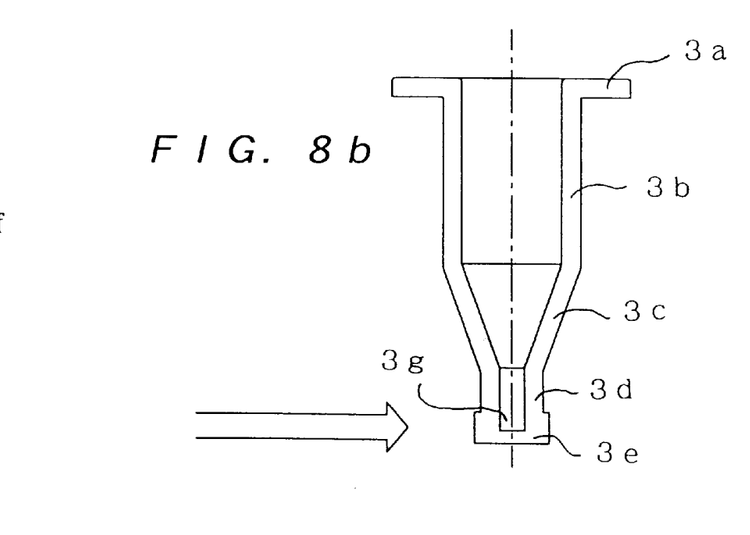
FIG. 8b is a cross-sectional view of the vessel.
Figure 8C:
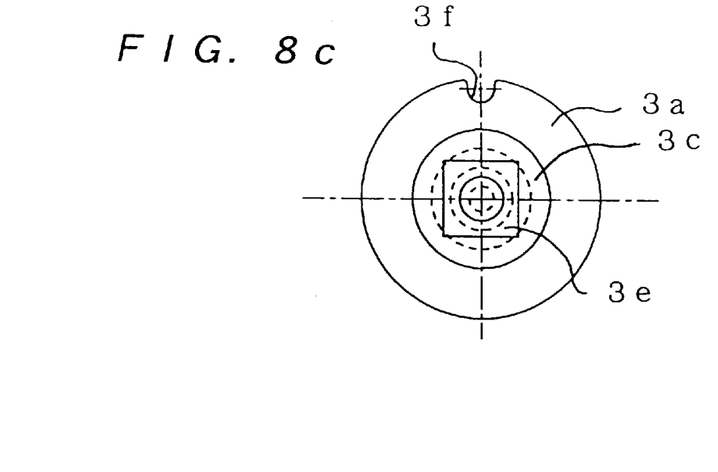
FIG. 8c is a bottom view of the vessel.

FIG. 8 shows a preferred embodiment of the imaging vessel 3, preferably formed as a one-piece molding of polystyrene resin. The vessel has a ring-shaped upper portion 3a having a notch 3f for positioning purposes. The imaging vessel 3 comprises a cylindrical portion 3b that extends vertically downward from the upper portion 3a to a small-diameter portion 3d, via a sloping portion 3c. A substantially square or rectangular block portion 3e is formed at the lower end. One side of the block portion 3e is arranged to be illuminated by a laser beam, indicated by the arrow. When fluorescent particles are to be imaged, the imaging vessel 3 is attached to the apparatus, with the notch 3f being used to position the imaging vessel 3. When the vessel 3 has been fitted into position, a flat face of the block portion 3e is perpendicular to the direction of laser beam illumination, forming the entry surface for the incident beam. Thus, the laser beam illuminates only the bottom portion 3g of the imaging vessel 3.

Figure 9:
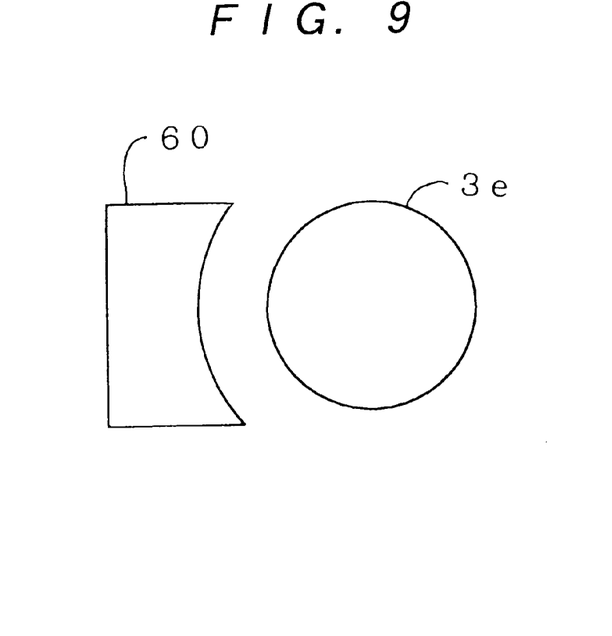
FIG. 9 is a cross-sectional horizontal view of an imaging vessel according to another configuration.

The bottom portion may also be illuminated by an arrangement such as the one shown in FIG. 9, in which the block portion 3e has a round cross-section, and a negative cylindrical lens 60 is disposed on the side from which the bottom portion is illuminated by the excitation beam.

Figure 10:
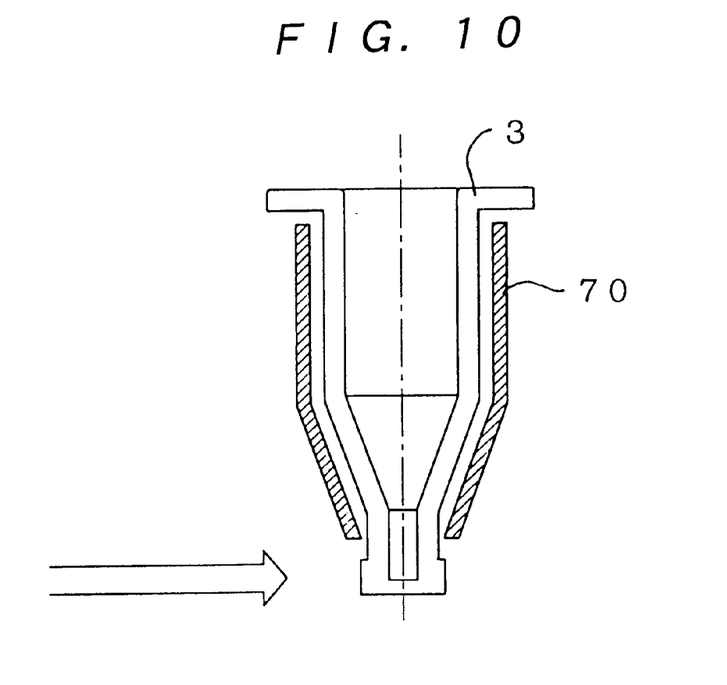
FIG. 10 is a cross-sectional view of an imaging vessel according to yet another configuration.

In the arrangement shown in FIG. 10, a cover 70 is used to shield parts of the imaging vessel 3 other than the bottom portion from the laser beam. In this case, the cover 20, shown in FIG. 3, on the imaging apparatus side may be omitted. The cover or shielding function may be realized by applying a light shield coating to the vessel, or by painting the vessel in a shielding color.

It is to be understood that while in the foregoing the invention has been described with reference to leukocytes as the fluorescent particles, the invention is not limited thereto but can be applied to other fluorescent particles.

As described in the foregoing, in accordance with the present invention, fluorescent particles to be imaged are collected in the bottom portion of the imaging vessel. Part of the exterior face of the bottom portion is an excitation light entry surface, so that only the bottom portion of the vessel is illuminated by the excitation light beam. Background light is thereby reduced, making it possible to obtain high-contrast images of the fluorescent particles contained in the vessel.

What is claimed is:

1. A vessel for imaging fluorescent particles that are stained with a fluorescent dye and illuminated by excitation light, the vessel comprising: a tubular body having an interior surface, an exterior surface, an upper portion, and a bottom portion having a side wall and a bottom wall for containing fluorescent particles, a part of the exterior surface of the tubular body corresponding to the bottom portion forming an entry surface for receiving a flat excitation beam or light projected generally parallel to the bottom wall of the bottom portion to illuminate the fluorescent particles to emit fluorescent light which is captured from the bottom wall for producing an image of the fluorescent particles.

2. A vessel for imaging fluorescent particles according to claim 1; further comprising a shielding member for covering exterior surface portions of the tubular body other than exterior surface portions thereof in a vicinity of the bottom wall of the bottom portion.

3. A vessel for imaging fluorescent particles according to claim 1; wherein the bottom portion of the tubular body has a generally square horizontal cross-section one side of which has a surface forming the entry surface for receiving the flat excitation beam of light.

4. A vessel for imaging fluorescent particles according to claim 1; wherein the bottom portion of the tubular body has a generally round horizontal cross-section.

5. A vessel for imaging fluorescent particles according to claim 1; wherein the bottom portion of the tubular body has a generally rectangular horizontal cross-section one side of which has a surface forming the entry surface for receiving the flat excitation beam of light.

6. A vessel for imaging fluorescent particles comprising: a tubular body having a lower section defining an interior space for containing fluorescent particles, the lower section having a side wall, a bottom wall and an exterior surface portion defining an entry surface for transmitting into the interior space a beam of light projected in a direction generally parallel to the bottom wall of the lower section to illuminate the fluorescent particles to emit fluorescent light which is captured from the bottom wall for producing an image of the fluorescent particles.

7. A vessel according to claim 6; further comprising a shielding member covering exterior surface portions of the tubular body other than the exterior surface portion of the lower section in the vicinity of the bottom wall.

8. A vessel according to claim 6; wherein the lower section of the tubular body has a generally square-shaped portion having a surface defining the entry surface for transmitting the beam of light into the interior space.

9. A vessel according to claim 6; wherein the lower section of the tubular body has a generally round-shaped portion having a surface defining the entry surface for transmitting the beam of light into the interior space.

10. A vessel according to claim 6; wherein the lower section of the tubular body has a generally rectangular-shaped portion having a surface forming the entry surface for transmitting the beam of light into the interior space.

* * * * *